US00PP23141P2

(12) United States Plant Patent
Bryson

(10) Patent No.: US PP23,141 P2
(45) Date of Patent: Oct. 23, 2012

(54) ***LOMANDRA* PLANT NAMED 'JB2LIME'**

(50) Latin Name: *Lomandra longifolia*
Varietal Denomination: JB2LIME

(76) Inventor: Craig Bryson, Wamberal (AU)

( * ) Notice: Subject to any disclaimer, the term of this patent is extended or adjusted under 35 U.S.C. 154(b) by 0 days.

(21) Appl. No.: 13/135,323

(22) Filed: Jun. 30, 2011

(51) Int. Cl.
*A01H 5/00* (2006.01)

(52) U.S. Cl. ..... Plt./373

(58) Field of Classification Search ..... Plt./373, Plt./263.1
See application file for complete search history.

*Primary Examiner* — Kent L Bell
(74) *Attorney, Agent, or Firm* — C. A. Whealy

(57) ABSTRACT

A new and distinct cultivar of *Lomandra* plant named 'JB2lime', characterized by its upright plant habit with foliage initially erect to outwardly arching; moderately vigorous growth habit; long lanceolate variegated leaves with yellow green and light yellow green-colored longitudinal stripes giving an overall lime green-colored appearance; and good garden performance.

2 Drawing Sheets

Botanical designation: *Lomandra longifolia.*
Cultivar denomination: 'JB2LIME'.

BACKGROUND OF THE INVENTION

The present invention relates to a new and distinct cultivar of *Lomandra* plant, botanically known as *Lomandra longifolia*, and hereinafter referred to by the name 'JB2lime'.

The new *Lomandra* plant is a naturally-occurring whole plant mutation of the *Lomandra longifolia* 'JB1glow', not patented. The new *Lomandra* plant was discovered and selected by the Inventor from within a population of plants of 'JB1glow' in a controlled greenhouse environment in Wamberal, New South Wales, Australia in 2007.

Asexual reproduction of the new *Lomandra* plant by micropropagated cuttings in Tumbi Umbi, New South Wales, Australia since 2007 has shown that the unique features of this new *Lomandra* plant are stable and reproduced true to type in successive generations.

SUMMARY OF THE INVENTION

Plants of the new *Lomandra* have not been observed under all possible environmental conditions and various cultural practices. The phenotype may vary somewhat with variations in environmental conditions such as temperature and light intensity, without, however, any variance in genotype.

The following traits have been repeatedly observed and are determined to be the unique characteristics of 'JB2lime'. These characteristics in combination distinguish 'JB2lime' as a new and distinct *Lomandra* plant:

1. Upright plant habit with foliage initially erect to outwardly arching.
2. Moderately vigorous growth habit.
3. Long lanceolate variegated leaves with yellow green and light yellow green-colored longitudinal stripes giving an overall lime green-colored appearance.
4. Good garden performance.

Plants of the new *Lomandra* differ from plants of the parent, 'JB1glow', primarily in leaf coloration as plants of 'JB1glow' have darker yellow green-colored leaves.

Plants of the new *Lomandra* can be compared to plants of *Lomandra longifolia* 'LMV100', not patented. In side-by-side comparisons conducted in Wamberal, New South Wales, Australia, plants of the new *Lomandra* differed primarily from plants of 'LMV100' in the following characteristics:

1. Plants of the new *Lomandra* had broader leaves than plants of 'LMV100'.
2. Plants of the new *Lomandra* and 'LMV100' differed in leaf coloration as plants of 'LMV100' had darker yellow green-colored leaves.

BRIEF DESCRIPTION OF THE PHOTOGRAPHS

The accompanying photographs illustrate the overall appearance of the new *Lomandra* plant showing the colors as true as it is reasonably possible to obtain in colored reproductions of this type. Colors in the photographs may differ slightly from the color values cited in the detailed botanical description which accurately describe the colors of the new *Lomandra* plant.

The photograph on the first sheet comprises a side perspective view of typical plants of 'JB2lime' grown in a container.

The photograph on the second sheet is a side perspective view of a single typical plant of 'JB2lime' grown in a container.

DETAILED BOTANICAL DESCRIPTION

The aforementioned photographs and following observations and measurements describe plants grown during the summer and autumn in 40-cm containers in an outdoor nursery in Wamberal, New South Wales, Australia and under conditions and practices which approximate those generally used in commercial *Lomandra* plant production. During the production of the plants, day temperatures ranged from 20° C. to 35° C. and night temperatures ranged from 10° C. to 18° C. Plants were 13 months old when the photographs and the botanical description were taken. In the following description, color references are made to The Royal Horticultural Society Colour Chart, 2007 Edition, except where general terms of ordinary dictionary significance are used.

Botanical classification: *Lomandra longifolia* 'JB2lime'.

Parentage: Naturally-occurring whole plant mutation of *Lomandra longifolia* 'JB1glow', not patented.

Propagation:

*Type*.—By micropropagated cuttings.

*Time to initiate roots, summer*.—About seven to ten days at temperatures of about 20° C. to 25° C.

*Time to initiate roots, winter*.—About ten days to two weeks at temperatures of about 15° C. to 20° C.

*Time to produce a rooted young plant, summer*.—About 25 to 30 days at temperatures of about 20° C. to 25° C.

*Time to produce a rooted young plant, winter*.—About 35 to 40 days at temperatures of about 15° C. to 20° C.

*Root description*.—Medium thickness, fibrous; white in color.

*Rooting habit*.—Moderately freely branching; dense.

*Rhizome length*.—About 3 cm to 4 cm.

*Rhizome texture*.—Smooth, glabrous.

*Rhizome color*.—Close to 155C.

Plant description:

*Plant and growth habit*.—Upright plant habit with foliage initially erect to outwardly arching; broadly inverted triangle; dense and bushy appearance; plants caespitose; leaf arrangement equitant with nine to twelve leaves per clump; moderately vigorous growth habit.

*Plant height*.—About 90 cm.

*Plant diameter or spread*.—About 80 cm.

*Shoot width at base*.—About 1.1 cm to 2.2 cm.

Foliage description:

*Orientation*.—Initially erect to outwardly arching; slightly twisting.

*Length*.—About 75 cm to 85 cm.

*Width*.—About 1.2 cm to 1.5 cm.

*Shape*.—Lanceolate.

*Apex*.—Emarginate; necrosis of apical tissue frequent.

*Margin*.—Entire.

*Cross-sectional profile*.—Towards the base, concave, flattening towards the apex.

*Texture, upper and lower surfaces*.—Leathery; corrugated, glabrous.

*Luster, upper and lower surfaces*.—Dull.

*Venation pattern*.—Parallel.

*Color*.—Developing leaves, upper and lower surfaces: Close to 145D. Fully expanded leaves, upper and lower surfaces: Longitudinal stripes, close to N144A and 144A; towards the base, close to 145D and 157C; overall appearance, lime green in color, close to 145A. Venation, upper and lower surfaces: Similar to surface coloration. Basal leaf sheath: Close to N199C to N199D.

Flower description: Flower initiation and development has not been observed on plants of the new *Lomandra*.

Disease/pest resistance: Plants of the new *Lomandra* have not been shown to be resistant to pathogens and pests common to *Lomandra*.

Keeping quality: Excellent keeping quality; plants of the new *Lomandra* are durable and will maintain good leaf substance indefinitely.

Garden performance: Plants of the new *Lomandra* have been observed to have good garden performance and to tolerate wind, rain and high temperatures of about 40° C. Low temperature tolerance has not been determined.

It is claimed:

1. A new and distinct *Lomandra* plant named 'JB2lime' as illustrated and described.

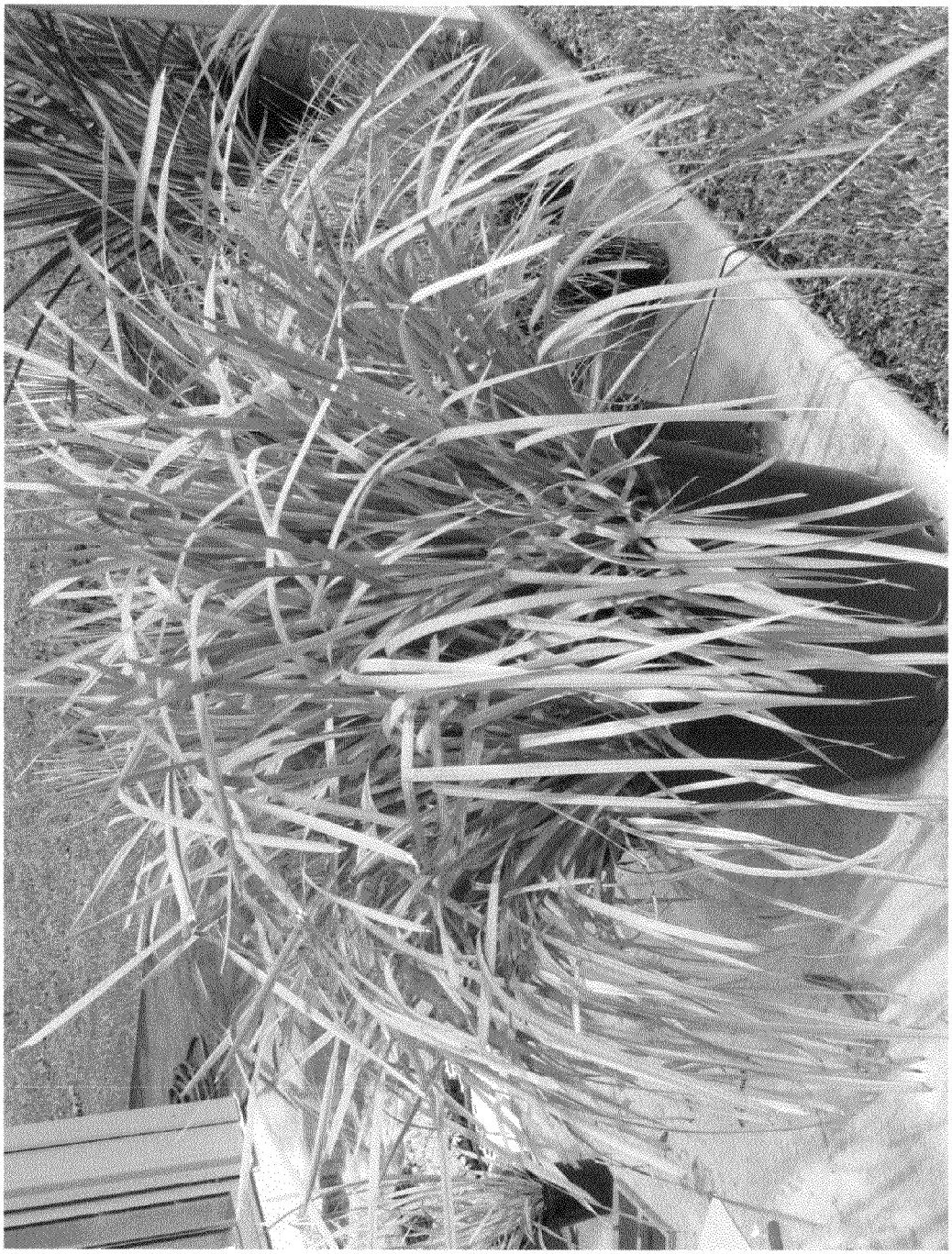

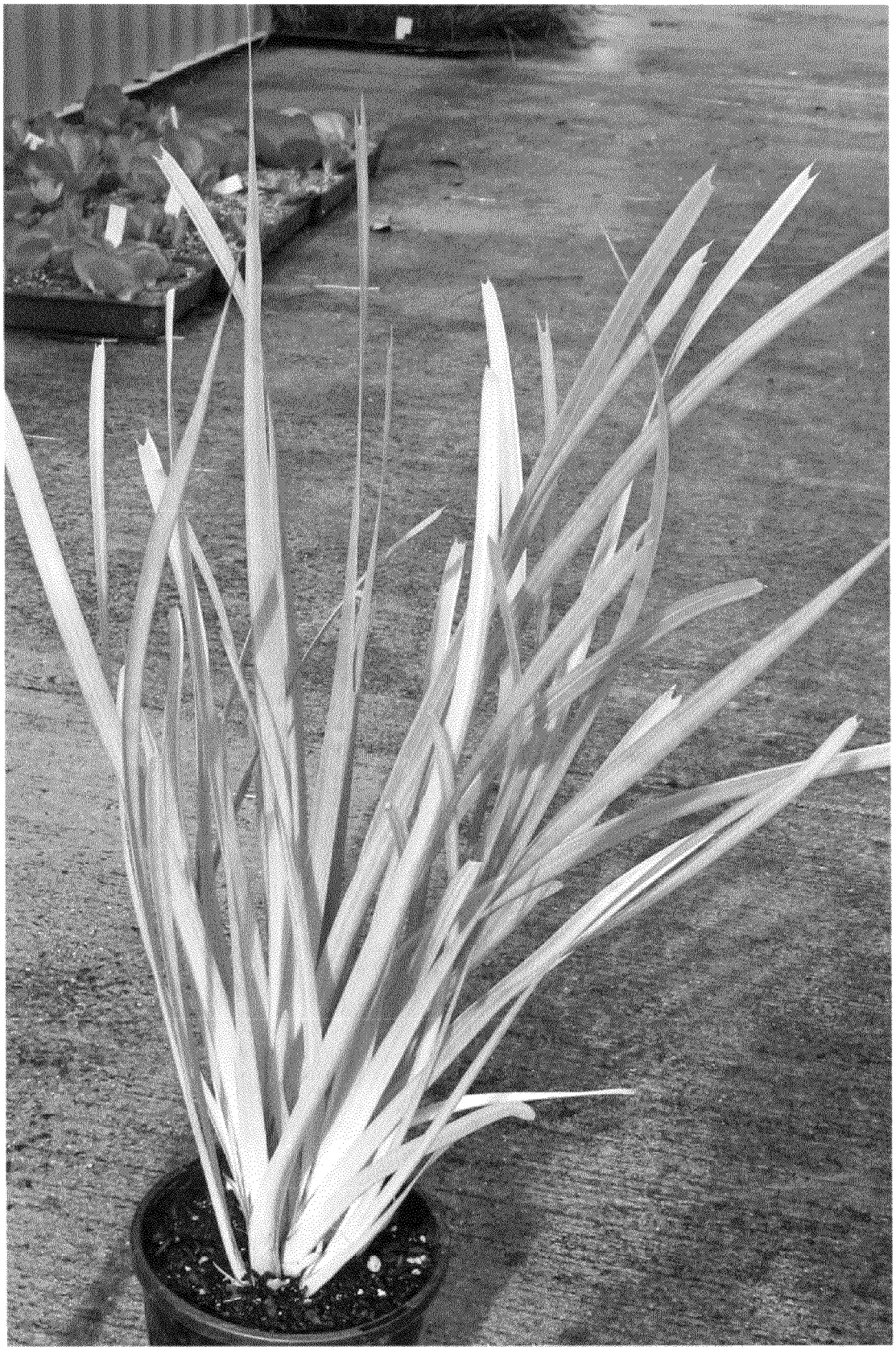

* * * * *